US009475514B2

(12) United States Patent
Hardy et al.

(10) Patent No.: US 9,475,514 B2
(45) Date of Patent: Oct. 25, 2016

(54) MEDICAL CARTS WITH TOUCH-SENSITIVE FOOT PANELS, AND ASSOCIATED APPARATUSES AND METHODS

(71) Applicant: Capsa Solutions, Portland, OR (US)

(72) Inventors: Rody Myron Hardy, Portland, OR (US); Adam William Landis, Reynoldsburg, OH (US); Timothy Charles Rothwell, Dublin, OH (US); Eric John Webb, Vancouver, WA (US)

(73) Assignee: CAPSA SOLUTIONS, Portland, OR (US)

( * ) Notice: Subject to any disclaimer, the term of this patent is extended or adjusted under 35 U.S.C. 154(b) by 0 days.

(21) Appl. No.: 14/538,564

(22) Filed: Nov. 11, 2014

(65) Prior Publication Data

US 2015/0166090 A1   Jun. 18, 2015

Related U.S. Application Data

(60) Provisional application No. 61/902,685, filed on Nov. 11, 2013.

(51) Int. Cl.
*B62B 3/00* (2006.01)
*B62B 3/02* (2006.01)
*A61G 12/00* (2006.01)

(52) U.S. Cl.
CPC ............. *B62B 3/02* (2013.01); *A61B 50/13* (2016.02); *A61B 50/15* (2016.02); *A61G 12/001* (2013.01); *A61G 2203/20* (2013.01); *B62B 2203/10* (2013.01); *B62B 2206/06* (2013.01)

(58) Field of Classification Search
CPC ............. B62B 3/02; B62B 3/10; B62B 3/00; B62B 5/04; B62B 5/0433; B62B 2203/10; B62B 2203/07; B62B 2202/56; B62B 2206/06; A47B 21/02; A61G 12/00; A61G 12/001; A61G 12/008; F16M 11/00; F16M 11/28; F16M 11/18; F16M 11/42; F16M 11/20; F16M 11/24; H01H 3/14; H01H 13/16
See application file for complete search history.

(56) References Cited

U.S. PATENT DOCUMENTS

| | | | | |
|---|---|---|---|---|
| 5,268,624 A | * | 12/1993 | Zanger | 318/551 |
| 6,343,556 B1 | * | 2/2002 | Lanphear | 108/147 |
| 6,437,682 B1 | * | 8/2002 | Vance | 338/185 |
| 6,874,432 B2 | * | 4/2005 | Lanphear | 108/147 |
| 6,962,581 B2 | * | 11/2005 | Thoe | 606/1 |
| 8,172,255 B1 | * | 5/2012 | Martin | 280/651 |
| 8,662,605 B2 | * | 3/2014 | McRorie et al. | 312/276 |
| 8,853,571 B2 | * | 10/2014 | Tseng | 200/86.5 |
| 9,039,016 B2 | * | 5/2015 | Abernethy et al. | 280/6.15 |

(Continued)

*Primary Examiner* — James M Dolak
(74) *Attorney, Agent, or Firm* — Perkins Coie LLP

(57) ABSTRACT

Embodiments of medical carts and associated apparatuses and methods are disclosed herein. A medical cart configured in accordance with one embodiment includes a cart base assembly, a work platform, and a height adjustment assembly carrying the work platform above the cart base assembly. The cart base assembly includes an upper portion and a touch-sensitive foot panel generally below the upper portion. The touch-sensitive foot panel includes a resilient cover having a contact surface and a contact switch underlying the resilient cover. The contact switch is operably coupled to the height adjustment assembly, and the contact switch is configured to detect for operator foot contact at the contact surface and to raise or lower the work platform via the height adjustment assembly when the operator foot contact is detected.

6 Claims, 8 Drawing Sheets

(56) References Cited

U.S. PATENT DOCUMENTS

| | | | |
|---|---|---|---|
| 9,198,816 B2 * | 12/2015 | Cipriano | |
| 9,240,110 B2 * | 1/2016 | Roth | H01H 3/14 |
| 9,242,664 B2 * | 1/2016 | Arceta | A61G 12/001 |
| 2008/0252045 A1 * | 10/2008 | Rossini et al. | 280/659 |
| 2010/0213679 A1 * | 8/2010 | Smith et al. | 280/47.35 |

* cited by examiner

MEDICAL CARTS WITH TOUCH-SENSITIVE FOOT PANELS, AND ASSOCIATED APPARATUSES AND METHODS

CROSS-REFERENCE TO RELATED APPLICATION

The present application claims priority to U.S. Provisional Application No. 61/902,685, filed Nov. 11, 2013, which is incorporated herein by reference in its entirety.

TECHNICAL FIELD

The present technology is related to medical carts. In particular, some embodiments are related to medical carts having a work platform and touch-sensitive foot panels configured to adjust vertical platform height.

BACKGROUND

Medical carts are configured to store, carry, and transport medical supplies, equipment, materials, and other items in a variety of different patient settings (e.g., doctor's office, hospital, etc.). For example, medical carts can carry and transport medications, ultrasound equipment, patient files, a laptop computer, and/or a variety of other types of medical supplies/equipment. Some medical carts also include a work platform that an operator can raise and lower to a desired position using an integrated vertical lift mechanism.

DETAILED DESCRIPTION

The following disclosure describes various types of medical carts and associated apparatuses and methods. Certain details are set forth in the following description and FIGS. 1-12 to provide a thorough understanding of various embodiments of the disclosure. Other details describing well-known structures and systems often associated with medical carts, however, are not set forth below to avoid unnecessarily obscuring the description of the various embodiments of the disclosure.

Many of the details and features shown in the Figures are merely illustrative of particular embodiments of the disclosure. Accordingly, other embodiments can have other details and features without departing from the spirit and scope of the present disclosure. In addition, those of ordinary skill in the art will understand that further embodiments can be practiced without several of the details described below. Furthermore, various embodiments of the disclosure can include structures other than those illustrated in the Figures and are expressly not limited to the structures shown in the Figures. Moreover, the various elements and features illustrated in the Figures may not be drawn to scale.

In the Figures, identical reference numbers identify identical or at least generally similar elements. To facilitate the discussion of any particular element, the most significant digit or digits of any reference number refer to the Figure in which that element is first introduced. For example, element 112 is first introduced and discussed with reference to FIG. 1.

Figure 1:
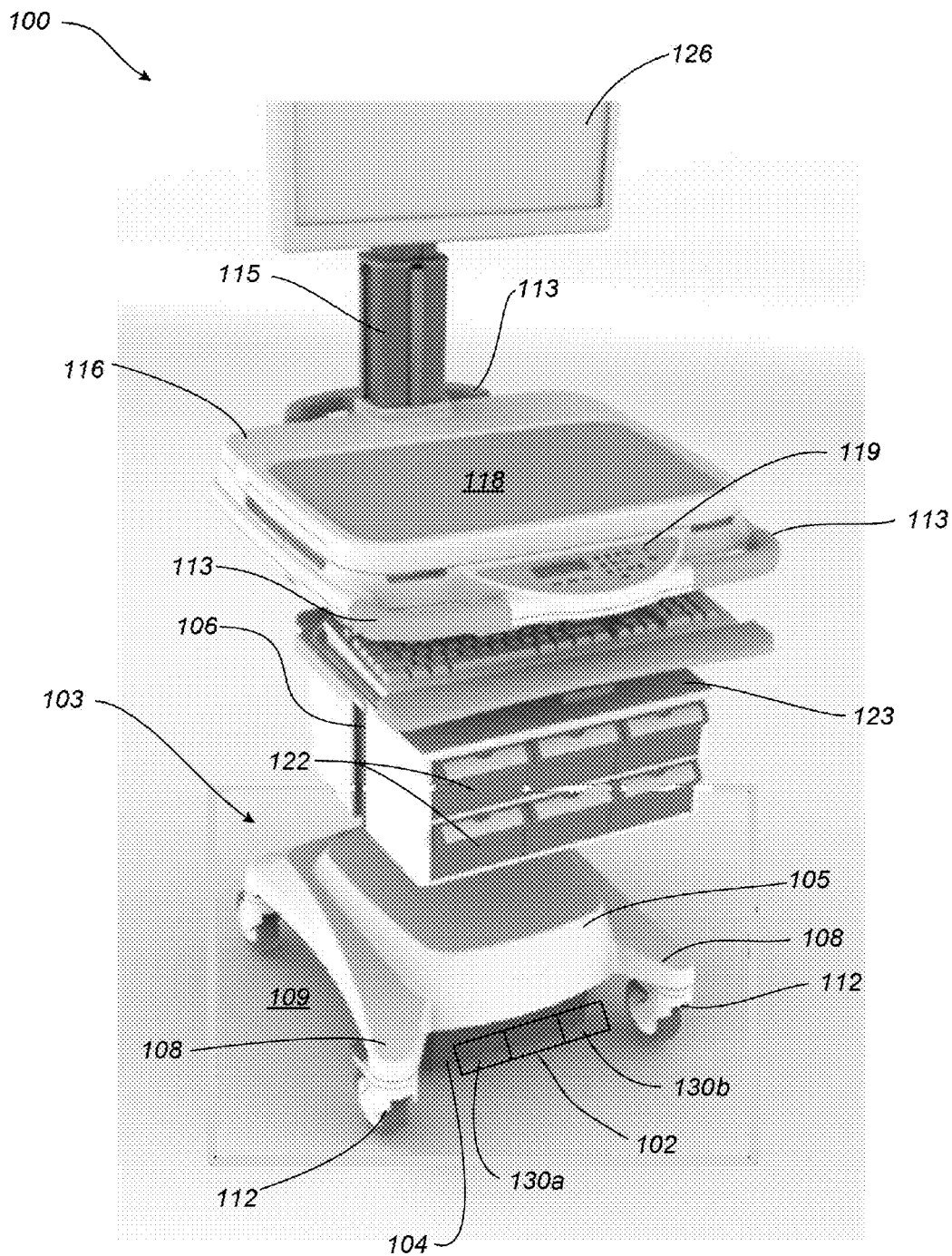
FIG. 1 is an isometric view of a medical cart having a cart base with a foot switch assembly configured in accordance with an embodiment of the present technology.

FIG. 1, for example, is an isometric view of medical cart 100 having a foot switch assembly 102 configured in accordance with an embodiment of the present technology. As shown, the medical cart 100 includes a cart base assembly or cart base 103 ("base 103") and a height adjustment assembly or actuator 115 (e.g., a linear actuator) carrying a work platform 116 above the cart base 103. The work platform 116 can include, for example, a work surface 118 for supporting, e.g., a laptop, medical instruments, patient files, etc., and handle portions 113 that an operator can use to facilitate positioning and transport of the medical cart 100. In the illustrated embodiment, the medical cart 100 further includes a monitor 126 and a storage module 123 having lockable compartments 122 (containing, e.g., medication, medical supplies, etc.) that can be individually opened and accessed via a keypad 119. Although not shown for purposes of clarity, the medical cart 100 can include additional and/or alternate components and/or accessories in other embodiments, such as a storage basket, additional platforms, tool holders, etc.

The cart base 103 includes an upper portion 105 (e.g., a support platform) and a plurality of leg portions 108 at the outer corners of the upper portion 105 and coupled to corresponding wheel assembles 112 (e.g., caster assemblies). In at least some embodiments, a storage compartment 104 can be located beneath the upper portion 105 for storing a power supply (e.g., a battery) configured to provide electrical power to the actuator 115 and/or other components of the medical cart 100 (e.g., the monitor 126). As further shown in FIG. 1, cart base 103 is configured to carry the foot switch assembly 102 above a floor surface 109.

The foot switch assembly 102 (shown schematically) is operably coupled to the actuator 115, and includes first and second touch-sensitive foot panels 130a and 130b (collectively "foot panels 130"). In operation, the foot switch assembly 102 is configured to raise or lower the work platform 106 via the actuator 115 when an operator engages one of the foot panels 130, such as by contacting either of the foot panels 130 with the operator's foot. In the illustrated embodiment, for example, contact with the first foot panel 130a will lower the work platform 116, while contact with the second foot panel 130b will raise the work platform 116. As described in greater detail below, the foot panels 130 can be configured to be touch sensitive and, in some embodiments, can operate with minimal contact force or substantially no contact force applied to the foot panels 130.

Figure 2A:
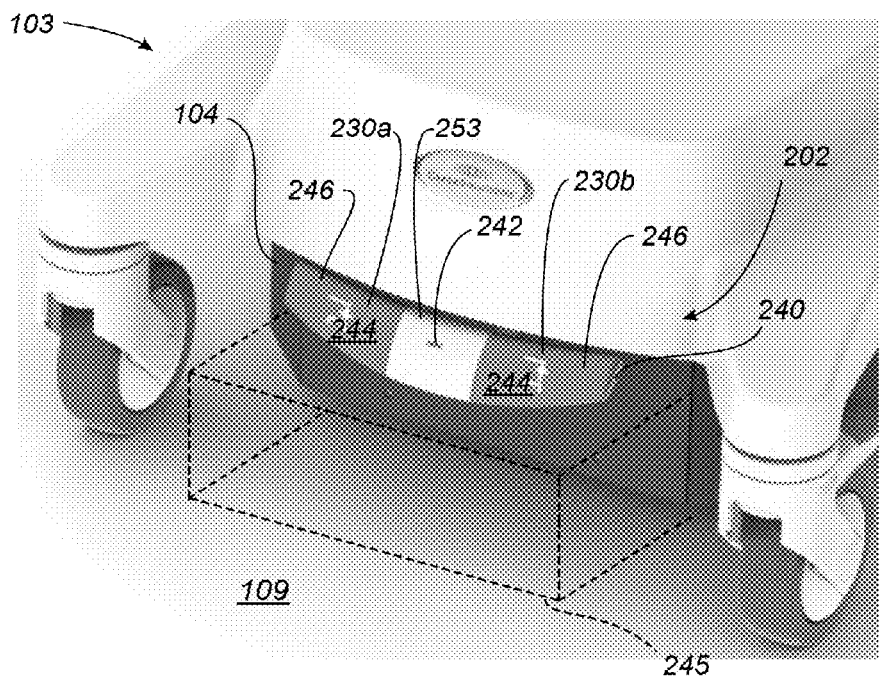
FIG. 2A is an isometric view of a foot switch assembly configured in accordance with an embodiment of the present technology.
Figure 2B:
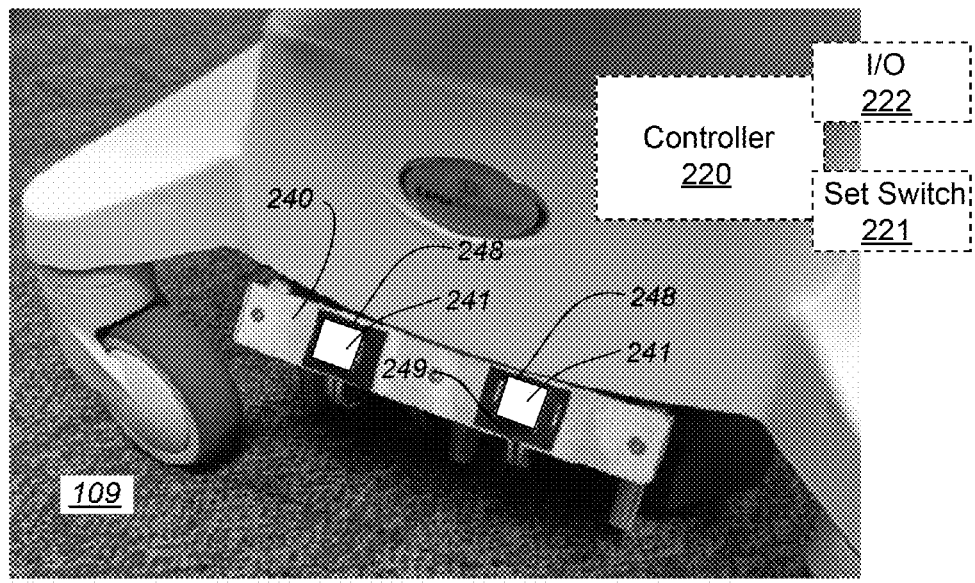
FIG. 2B is an isometric view of the foot switch assembly of FIG. 2A with an outer cover removed.

FIG. 2A is an isometric view of a foot switch assembly 202 configured in accordance with an embodiment of the present technology. FIG. 2B is an isometric view of the foot switch assembly 202 with an outer cover of the switch assembly 202 removed for purposes of illustration. Referring to FIGS. 2A and 2B together, the foot switch assembly 202 includes a support structure 240 located generally below the upper portion 105 of the cart base 103, and first and second foot panels 230a and 230b (collectively "foot panels 230") located on the support structure 240. In the illustrated embodiment, the foot switch assembly 202 includes a light-emitting element 242 (e.g., a light emitting diode) located on the support structure 240 and between the foot panels 230. In at least some embodiments, the light-emitting element 242 can be configured to indicate whether the cart base 103 is powered on, a battery is charging, a fault condition has occurred, etc.

The support structure 240 is configured to position the foot panels 230 in a forward facing direction and inclined relative to a contact or approach angle of an operator's foot. For example, the angle of the support structure 240 relative to a floor surface 109 can be based on an average foot size and/or position of a heel on the floor surface 109. In one aspect of this embodiment, the switch assembly 102 is positioned above a stride space 245 (represented by broken lines) of an operator. In one embodiment, the stride space 245 can provide, e.g., 5 to 10 cm of clearance between the floor surface 109 and the bottom portion of the foot switch assembly 102. When positioned above the stride space 245 in such a manner, an operator's feet can move beneath the cart base 103 when transporting or otherwise moving medical cart 100, which helps prevent inadvertent foot contact with the foot panels 230 as the operator's feet move into and out of the stride space 245. In another embodiment, the height of the stride space 245 above the floor surface 109 can be selected such that the operator can comfortably operate the foot panels 230 with the heel of the foot positioned on the floor surface 109.

As further shown in FIGS. 2A and 2B, each of the foot panels 230 can include a resilient cover portion 246 (FIG. 2A) covering an underlying contact switch 248 (FIG. 2B) and including a contact surface 244. The contact switch 248 is configured to be actuated upon foot contact with the contact surface 244 of the overlying cover 246. In at least some embodiments, the contact switch 248 and the resilient cover 246 are configured such that the operator need apply only minimal or virtually no contact force to actuate the foot panel. For example, in one embodiment, the contact switch 248 and the resilient cover 246 can be configured such that the foot panel is actuated by lateral and/or vertical forces in the range of from about, e.g., 1.0 lbf to about 10 lbf. In another embodiment, virtually no contact force is needed to actuate either of the foot panels 230. In at least some embodiments, the contact switch 248 can include a flat, non-tactile printed circuit (e.g., a silver flat circuit) configured to be extremely sensitive to contact forces, while the resilient cover 246 can provide a protective cover that distributes forces across the surface of the printed circuit. In selected embodiments, the contact switch 248 can include a FlexiForce® Load/Force Sensor, available from Tekscan, Inc. of 307 West First Street, South Boston, Mass. 02127-1309. In other embodiments, the contact switch 248 can include a SensTouch™ switch from MaxTech Circuit of 427 7th Ave South, Kirkland Wash. 98033. The resilient cover 246 can include, for example, a rubber or plastic membrane, shell, or other overlying material, such as polyester and/or other suitable elastomeric or non-elastomeric materials, that can be adhered, fastened, or otherwise attached to the support structure 240. In at least some embodiments, the contact surface 244 can include, a graphical icon, text, and/or another indicia at its outer surface indicating a direction of vertical movement (e.g., up or down).

In the illustrated embodiment, the contact switches 248 are operably coupled to a controller 220 (e.g., a microcontroller; shown schematically). The controller 220 can include a programmable processor configured to execute instructions in memory, such as random access memory (RAM), read only memory (ROM), and/or other non-volatile memory, in order to perform various processes, logic flows, and routines. In one embodiment, the controller 220 can store calibration parameters, such as a parameter corresponding to a minimum contact force, or touch-sensitivity threshold, necessary to engage the foot panels 230. For example, in one embodiment, a user can calibrate the touch-sensitivity of the foot panels 230 to a particular touch-sensitivity threshold having a value between, e.g., about 0 lbf to about 50 lbf. In these and other embodiments, the foot switch assembly 202 can include a set switch 221 (shown schematically) or other adjustment feature (e.g., a knob) that allows the operator to set or change the touch-sensitivity. In addition or alternately, the foot switch assembly 102 may further include a USB or other communication port 222 that allows an operator to change the touch-sensitivity with an external control/computing device.

In at least some embodiments, the foot panels 230 are configured to momentarily actuate the actuator 115 (FIG. 1) such that once the operator's foot is out of contact with a particular one of the foot panels 230, the actuator 115 ceases upward or downward movement of the work platform 116. In certain embodiments, the vertical lift speed of the actuator 115 can vary depending on the duration of contact with the foot panels 230. For example, a short duration of foot contact can produce a relatively slow speed, while a longer duration can gradually increase the lift speed. In still further embodiments, the foot panels 230 can be configured to modulate the vertical lift speed based on foot pressure (with, e.g., additional foot pressure increasing speed).

As best seen in FIG. 2A, a non-contact portion 253 of the foot switch assembly 202 can be composed of the same material as the resilient cover portions 246, but can have a different color, texture, and/or other feature, such as a different thickness than the resilient cover portions 246. In still further embodiments, the non-contact portion 253 can be generally identical in composition, thickness, color, etc. as the resilient cover portions 246. For example, the non-contact and resilient cover portions 246, 253 can be a single piece of material that covers the outwardly facing portion of the support structure 240. In other embodiments, the non-contact portion 253 can be composed of a different material than the resilient cover portions 246, such as metal, hard plastic, or other protective materials.

In at least some embodiments, the foot panels 230 can include a back light, a light pipe, or other light emitting feature (e.g., a phosphorescent feature) that emits light from at least a portion of the resilient cover 246. In some embodiments, the foot panels 230 can emit light automatically in low light environments. For example, the foot switch assembly 202 can include an optical sensor (not shown) that turns off light emission when it detects ambient light. In other embodiments, the foot switch assembly 202 can include a switch (not shown) to activate light emission. In still further embodiments, the foot panels 230 may remain illuminated while the medical cart 100 (FIG. 1) powered on regardless of ambient light conditions.

Figure 3:
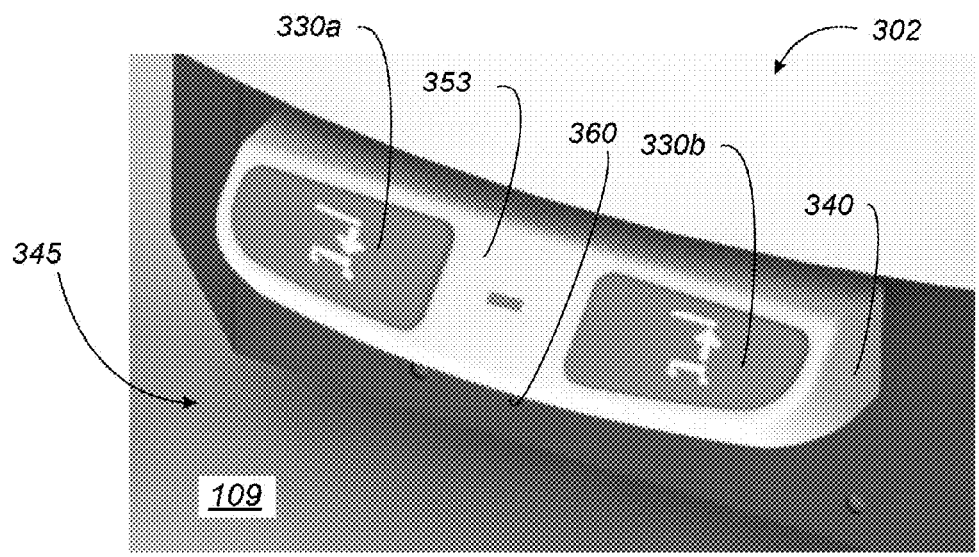
FIGS. 3-12 show switch assemblies having various configurations of support structures, foot panels, and other features configured in accordance with various embodiments of the present technology.

FIGS. 3-12 show switch assemblies and various configurations of support structures, foot panels, and other features configured in accordance with various embodiments of the present technology. Referring first to FIG. 3, for example, a foot switch assembly 302 includes a support structure 340 having foot panels 330 that are offset from a peripheral edge 360 of the support structure 340. In one aspect of this embodiment, the peripheral edge 360 can stop an operator's upwardly or downwardly moving foot within the stride space 345 from inadvertently contacting the foot panels 330. In another aspect of this embodiment, the foot panels 330 are elevated relative to the non-contact portion 353. This feature is expected to help an operator verify foot placement without looking at the foot panels 330. For example, the operator can move a foot toward the support structure 340 and sense the difference in surface height between the non-contact portion 353 and the foot panels 330.

Figure 4:
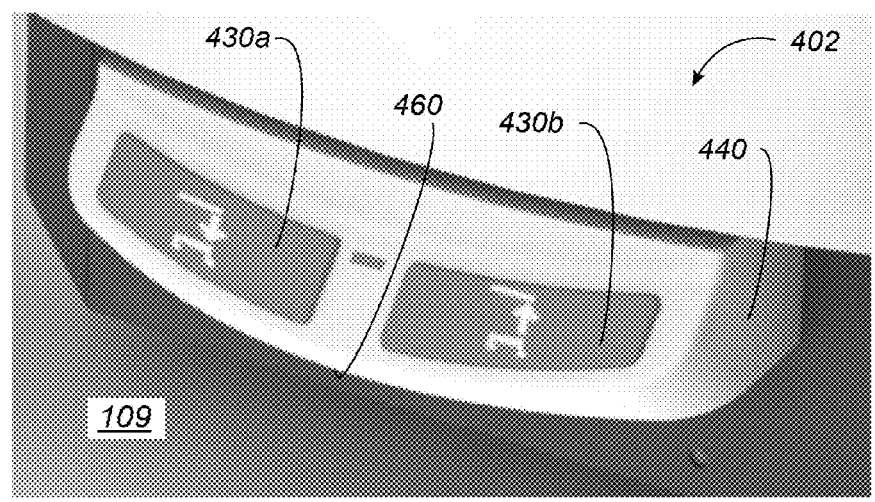
Figure 5:
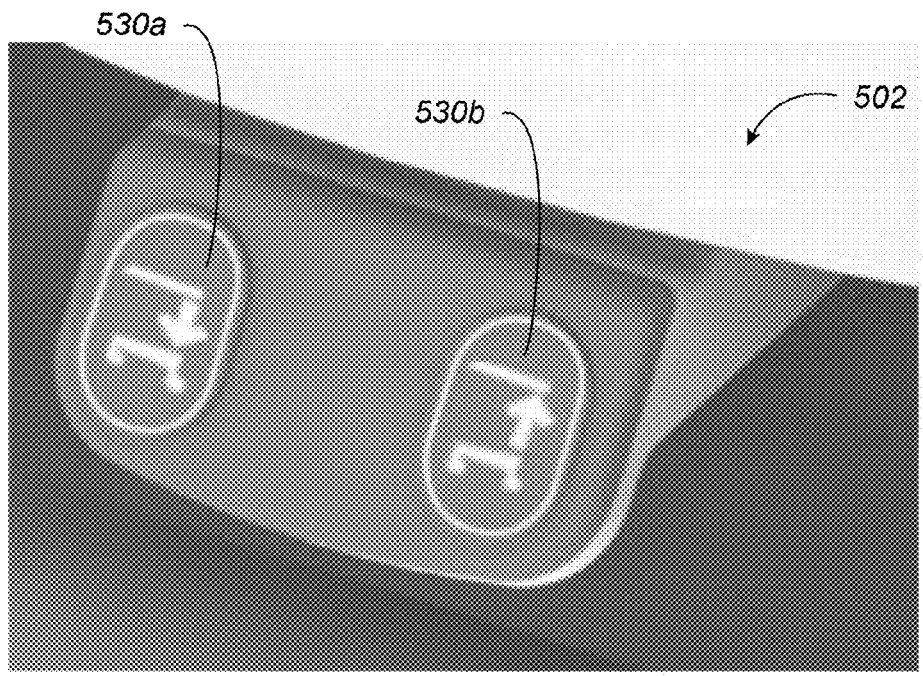
Figure 6:
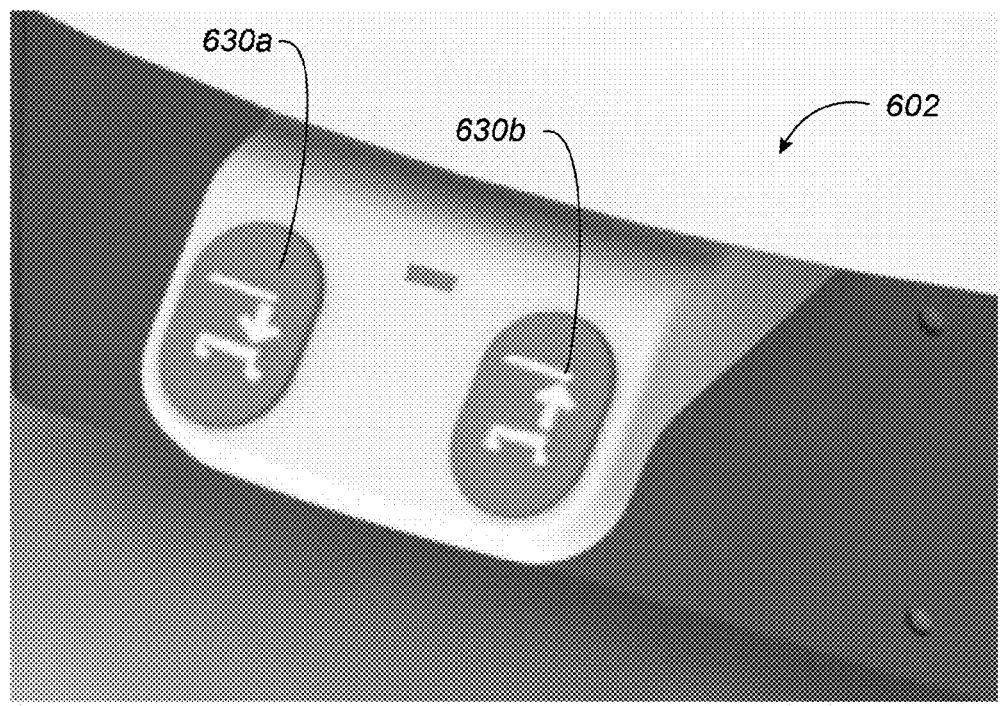

FIG. 4 shows a foot switch assembly 402 with features similar to the switch assembly 302 of FIG. 3. For example, the foot switch assembly 402 includes a support structure 440 having foot panels 430 that are offset from a peripheral edge 460 of support structure 440. In the arrangement of FIG. 4, however, the support structure 440 positions the foot panels 430 at a shallower angle relative to the floor surface 109. FIGS. 5 and 6 show, respectively, switch assemblies 502, 602 that also include features similar to the foot switch assembly 302 of FIG. 3, but include foot panels 530, 630 that are more elongated than the foot panels 330 of FIG. 3.

Figure 7:
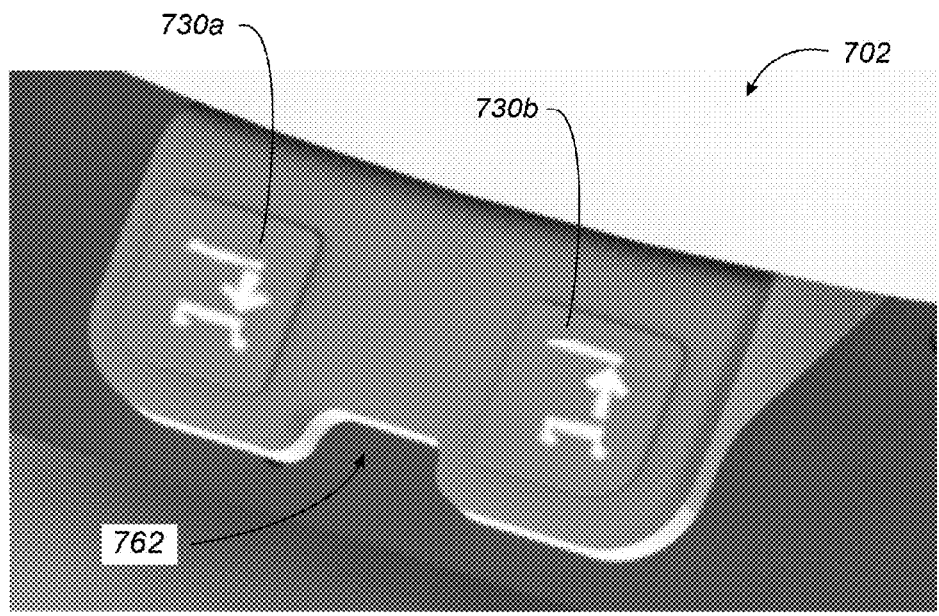
Figure 8:
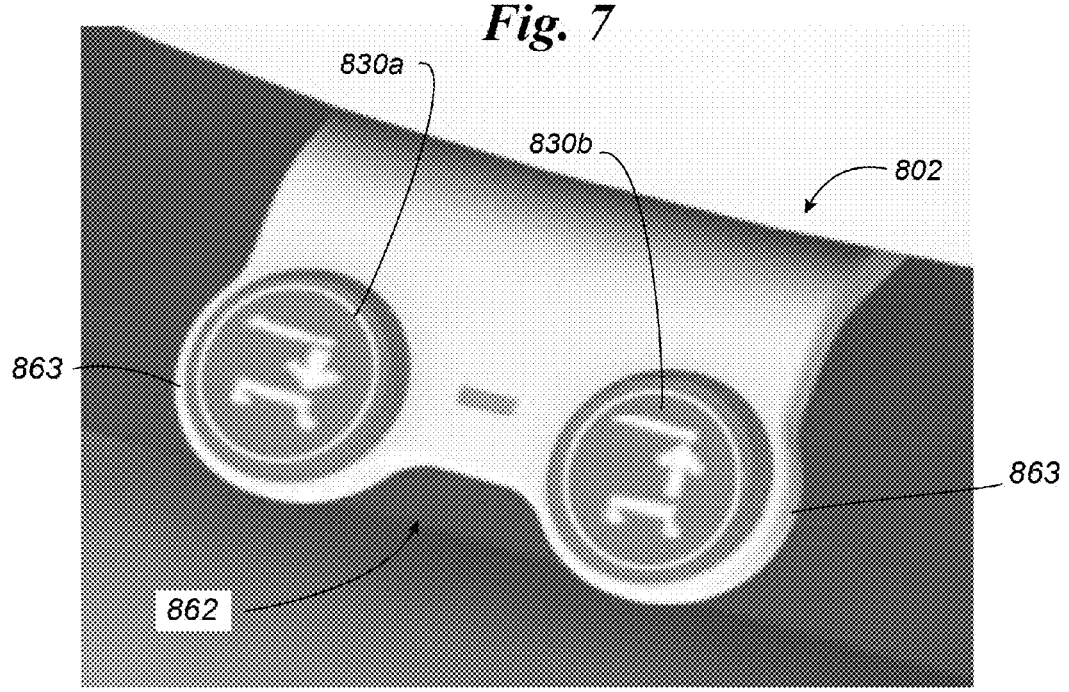
Figure 9:
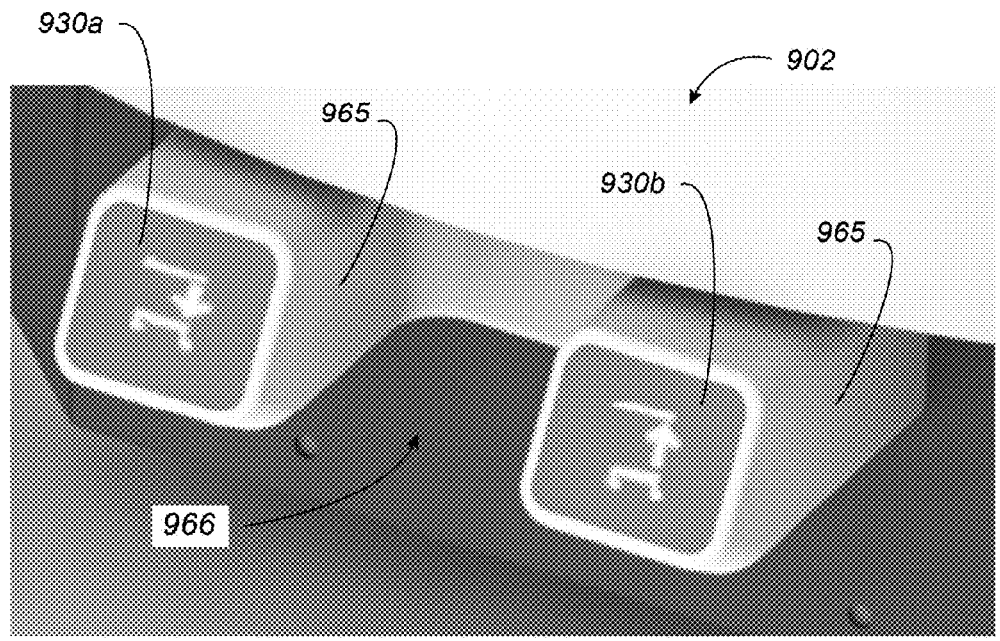

FIG. 7-9 show foot switch assemblies with contours or gaps in their respective support structures. Referring first to FIG. 7, for example, a foot switch assembly 702 includes a central contour 762 that extends toward a medial portion of a support structure 740. Similarly, FIG. 8 shows a foot switch assembly 802 having a support structure 840 with a central contour 862 and circular contours 863 that conform to the shape of circular foot panels 830. FIG. 9, on the other hand, includes a foot switch assembly 902 with arms 965 that each carry a foot panel 930 and are spaced apart by a gap 966 between the arms 965. In some embodiments, the contours and gaps of the embodiments illustrated in FIGS. 7-9 may help optimize stride space and/or help an operator verify foot contact with the foot panels.

Figure 10:
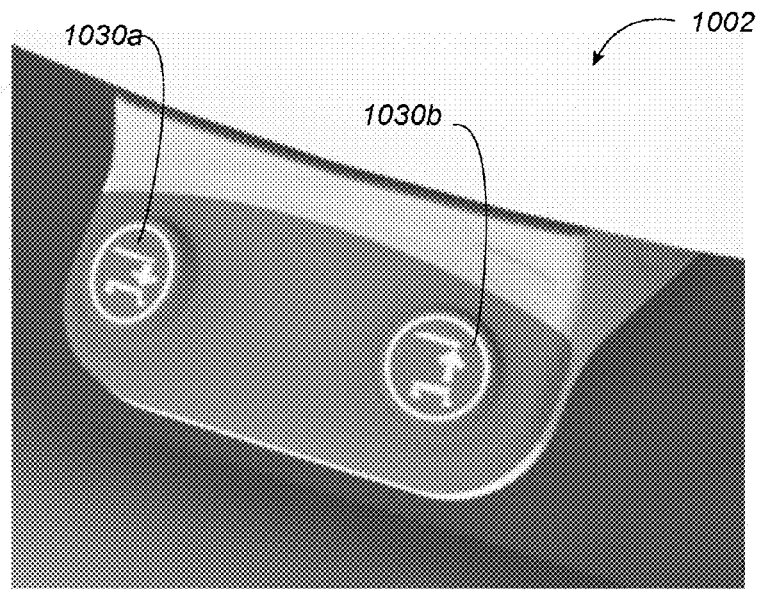

FIG. 10 shows a foot switch assembly 1002 comprising a support structure 1040 that curves outwardly (toward the operator) at a center region of the support structure 140. In this configuration, first and second foot panels 1030*a*, 1030*b* are non-coplanar and can be angled toward each particular foot of the operator. For example, the first foot panel 1030*a* can be angled toward a left foot of the operator and the second foot panel 1030*b* can be angled toward a right foot operator.

Figure 11A:
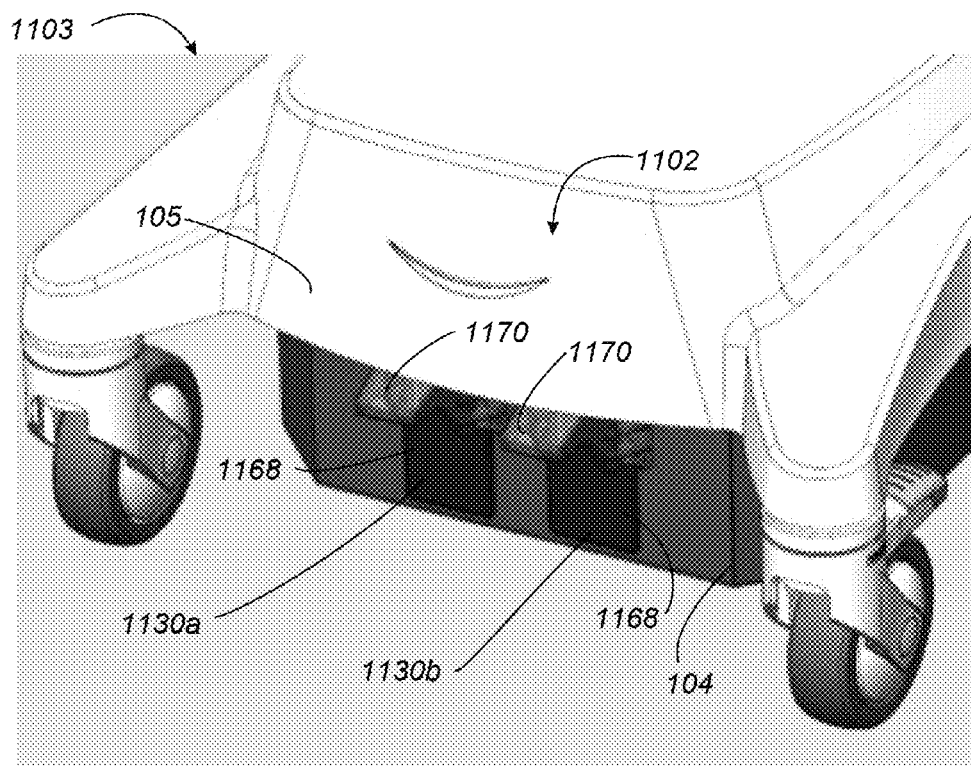
Figure 11B:
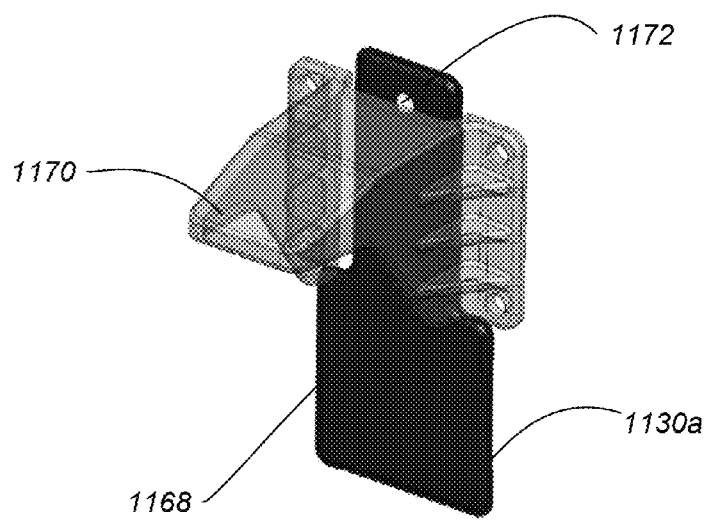

FIGS. 11A and 11B show a cart base assembly 1103 ("cart base 1103") having foot panels 1130 that are recessed beneath the cart base 103. In the illustrated embodiment, the unitary support structure is omitted, and the foot panels 1130 include an overlay 1168 (e.g., a polyester or plastic overlay) covering a contact switch (not shown) positioned on an outer surface of the compartment 104. The cart base 1103 may also include individual canopy structures 1170 aligned to each one of the foot panels 1130 and projecting beyond the cart base 1103. In this configuration, the canopy structures 1170 are visible to the operator from a downward viewing angle, but the foot panels 1130 themselves are not. In use, the canopy structure 1170 can provide a visual cue directing the operator to the location of the individual foot panels 1130 beneath the cart base 1103. In the illustrated embodiment, the canopy structure 1170 includes a translucent material optically coupled (i.e., as a light pipe) to a light feature 1172 (e.g., an LED) adjacent to the individual foot panels 1130. In other embodiments, however, the canopy structure 1170 can have other configurations, such as configuration in which it does not emit light. For example, a canopy structure can have a shape, size, and/or color (e.g., bright orange) that provides a suitable visual cue.

Figure 12:
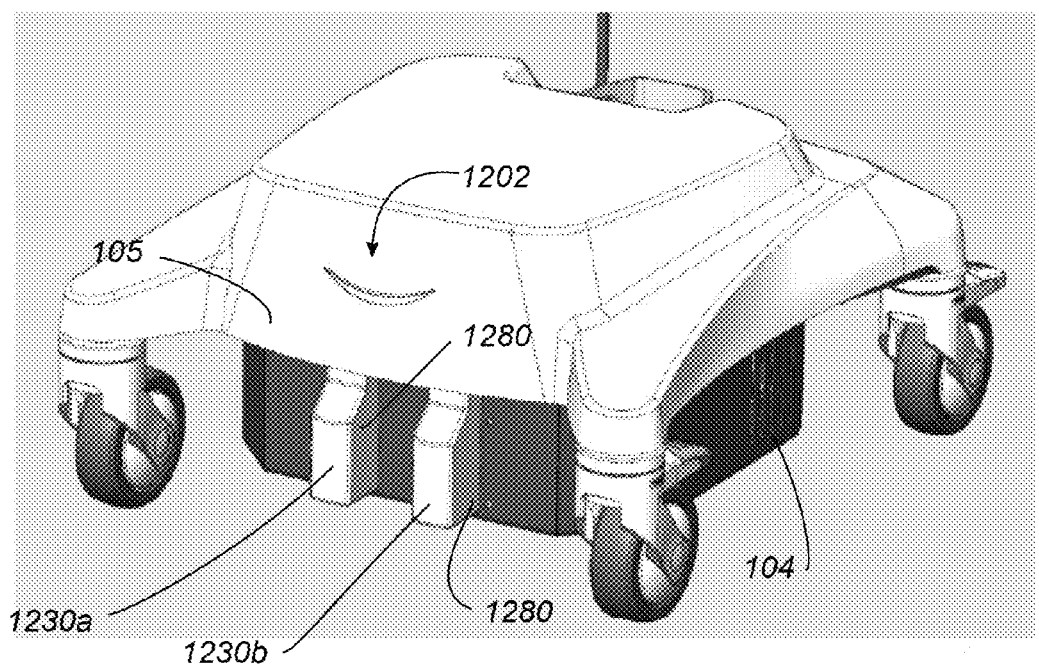

FIG. 12 shows a foot switch assembly 1202 having foot panels 1230 that are partially recessed beneath the cart base 103. In the embodiment shown in FIG. 12, the unitary support structure is omitted, and each of the foot panels 1230 is located on a separate, discrete support structure 1280. In some embodiments, the support structure 1280 can be attached to or integrated with a contact switch, such as the contact switch 248 described above with reference to FIGS. 2A and 2B. For example, a contact switch can be positioned between each of the support structures 1280 and the compartment 104.

From the foregoing, it will be appreciated that specific embodiments of the disclosure have been described herein for purposes of illustration, but that various modifications may be made without deviating from the spirit and scope of the various embodiments of the present technology. For example, rather than being on the left-hand side of the foot switch assembly 102 of FIG. 1, the first foot panel 130*a* of can be positioned on the right-hand side. In addition, although shown at a forward side of the cart base 103 (i.e., facing the operator), in some embodiments, the foot panels 130 can be positioned at different sides of the cart base 103, such as a rearward side. Further, while various advantages and features associated with certain embodiments of the disclosure have been described above in the context of those embodiments, other embodiments may also exhibit such advantages and/or features, and not all embodiments need necessarily exhibit such advantages and/or features to fall within the scope of the disclosure.

We claim:

1. A medical cart, comprising:
    a cart base assembly including a support platform, a first pressure-sensitive foot panel having a first contact switch, a second pressure-sensitive foot panel having a second contact switch, and a support structure positioning the first and second foot panels generally below the support platform, wherein the first foot panel includes a resilient cover having a first contact surface, and the first contact switch underlies a portion of the first contact surface, wherein the resilient cover is a single piece of resilient material covering the first and second switches, wherein the resilient material includes a non-contact portion between the first and second foot panels, and a portion having a second contact surface overlying the second contact switch, and wherein the support structure positions the first contact surface in a forward-facing direction that faces away from the support platform, and the second contact surface in a forward-facing direction that faces away from the support platform;
    a work platform;
    a height adjustment assembly carrying the work platform above the cart base assembly, wherein the height adjustment assembly includes a linear actuator for vertically lifting the work platform relative to the support platform; and
    a controller operably coupled to the linear actuator and the contact switch, wherein the controller is configured to:
    detect for operator foot contact at the first contact surface via the first contact switch, and
    raise the work platform via the linear actuator when operator foot contact is detected via the first contact switch,
    detect for operator foot contact at the second contact surface via the second contact switch, and
    lower the work platform via the linear actuator when operator foot contact is detected via the second contact switch.

2. The medical cart of claim 1 wherein the contact switch includes a printed circuit.

3. The medical cart of claim 1 wherein:
the controller is configured to move the work platform via the linear actuator at a first vertical lift speed in response to a first duration of operator foot contact with the first contact surface; and
the controller is configured to move the work platform via the linear actuator at a second vertical speed greater than the first vertical lift speed in response to a second duration of operator foot contact with the first contact surface, wherein the second duration is greater than the first duration.

4. The medical cart of claim 1, wherein:
the first foot panel is angled toward a left foot position of an operator; and
the second foot panel is angled toward a right foot position of an operator.

5. The medical cart of claim 1 wherein the support structure carries the foot panel above an operator stride space, and wherein the first contact surface is inclined relative to a floor surface below the operator stride space.

6. The medical cart of claim 1, further comprising a canopy structure projecting from the support platform and located above the foot panel, wherein the canopy structure is configured to provide a visual cue that directs the operator to a location of the foot panel beneath the cart base assembly.

* * * * *